United States Patent
Pageat (10) Patent No.: US 10,258,594 B2
(45) Date of Patent: *Apr. 16, 2019

(54) CAT APPEASING PHEROMONE (71) Applicant: INSTITUT DE RECHERCHE EN SEMIOCHIMIE ET ETHOLOGIE APPLIQUEE, Saint Saturnin d'apt (FR)

(72) Inventor: Patrick Pageat, Apt (FR)

(73) Assignee: INSTITUT DE RECHERCHE EN SEMIOCHIMIE ET ETHOLOGIE APPLIQUEE, Saint Saturnin d'Apt (FR)

(*) Notice: Subject to any disclaimer, the term of this patent is extended or adjusted under 35 U.S.C. 154(b) by 46 days.

This patent is subject to a terminal disclaimer.

(21) Appl. No.: 15/127,256

(22) PCT Filed: Mar. 17, 2015

(86) PCT No.: PCT/IB2015/000495
§ 371 (c)(1),
(2) Date: Sep. 19, 2016

(87) PCT Pub. No.: WO2015/140631
PCT Pub. Date: Sep. 24, 2015

(65) Prior Publication Data
US 2018/0169054 A1 Jun. 21, 2018

Related U.S. Application Data (60) Provisional application No. 61/954,771, filed on Mar. 18, 2014.

(51) Int. Cl.
| | |
|---|---|
| A61K 9/00 | (2006.01) |
| A61K 31/23 | (2006.01) |
| A61K 35/55 | (2015.01) |
| A61K 47/10 | (2017.01) |
| A61P 25/22 | (2006.01) |
| A61K 31/231 | (2006.01) |

(52) U.S. Cl.
CPC .......... *A61K 31/231* (2013.01); *A61K 9/0017* (2013.01); *A61K 31/23* (2013.01); *A61K 35/55* (2013.01); *A61K 47/10* (2013.01); *A61P 25/22* (2018.01); *A61K 2300/00* (2013.01)

(58) Field of Classification Search
USPC ........................................................ 514/549
See application file for complete search history.

(56) References Cited

U.S. PATENT DOCUMENTS

| | | |
|---|---|---|
| 6,054,481 A | 4/2000 | Pageat |
| 6,384,252 B1 | 5/2002 | Pageat |
| 6,500,862 B1 | 12/2002 | Zanello |
| 8,933,126 B2 | 1/2015 | Deminiere et al. |
| 8,980,309 B2 | 3/2015 | Carrara et al. |
| 2011/0077301 A1 | 3/2011 | Deminiere et al. |
| 2013/0261193 A1 | 10/2013 | Nouvel et al. |

FOREIGN PATENT DOCUMENTS

| | | |
|---|---|---|
| JP | H11-209293 | 8/1999 |
| JP | 2003-313104 | 11/2003 |
| JP | 2007-508261 | 4/2007 |
| WO | 96/23414 A1 | 8/1996 |
| WO | 99/37297 A1 | 7/1999 |
| WO | 2004/000336 A1 | 12/2003 |
| WO | 2009-144321 | 12/2009 |

OTHER PUBLICATIONS

"Feliway." 2012. XP055201604. Retrieved from internet on Jul. 10, 2015. http://www.gnpd.com.
International Search Report (ISR), dated Jul. 21, 2015, from corresponding PCT Application No. PCT/IB2015/000495.
International Preliminary Report on Patentability (IPRP), dated Sep. 20, 2016, from corresponding PCT Application No. PCT/IB2015/000495.

*Primary Examiner* — Kathrien A Cruz
(74) *Attorney, Agent, or Firm* — Young & Thompson (57) ABSTRACT

Disclosed is a semiochemical composition including methyl palmitate, methyl linoleate, methyl oleate methyl stearate, methyl laurate, methyl myristate, salts thereof, derivatives thereof, isomers thereof and/or structural analogues thereof that have an appeasing effect in cats and/or also effects social facilitation in cats, and an acceptable vehicle. Solutions such as spot-on formulations of long duration are also encompassed. Methods to effect appeasing in a cat and/or social facilitation in cats are also disclosed.

12 Claims, 3 Drawing Sheets

FIG. 3

Phase 0 :   Preparation of two cats
            Treatment of cats with cat appeasing pheromone or placebo.

Phase 1 :   Open the cages and liberate the cats in the hallway
            Let the cats roam for 5 minutes.

Phase 2 :   Observe the cats for 5 minutes in the hallway.

Phase 3 :   Introduction of the conflict of interest:
            A bowl with food Phase 4 :   Observe the conflict for : 5 min Phase 5 :   Take away the food and observe the cats for : 5 min The total duration for each test was : P0 10min + P1 5min + P2 5 min + P3 + P4 5min + P5= 30 minutes total

CAT APPEASING PHEROMONE

FIELD OF THE INVENTION

The present invention relates to a semiochemical composition comprising methyl palmitate, methyl linoleate, methyl, oleate, methyl stearate, methyl laureate, methyl myristate, salts thereof, derivatives thereof, isomers thereof and/or structural analogues that have an appeasing effect in cats or effects social facilitation in cats and an acceptable vehicle. Solutions such as spot-on formulations of long duration are also encompassed by the invention. Methods to effect appeasing in a cat and/or social facilitation in cats are also disclosed.

BACKGROUND AND PRIOR ART

There are several ways that cats communicate such as visual communication that communicate moods and interactions. These visual signal's include body posture, expressions, pupil size, the erection of hair and the tail position. It is well known that that the tail up position signals friendly intent when the cat approaches another animal or human, while tail down tucked between the legs often signals nervousness and/or submission. Tactile communication is when cats rub parts of their bodies against one another, touch noses and rest, or curl, up together. This is a form of social bonding between cats. Vocal communications have been classified as agonistic interactions, sexual interactions, mother-kitten interactions and cat-human interactions. Cats are said to have one of the largest different patterns of vocalization of all carnivore species. Olfactory communications in cats is used extensively for communication. Olfactory communication can be through depositing of urine and feces, through rubbing of their skin and through scratching of their paws.

Cats are most loving and well behaved when they are in control of their environment. This control is lost, however when owners move furniture, bring new furniture into a cats environment, via excessive cleaning, moving and adding an additional cat to the household. When the cats environment is interrupted, cats become disoriented, which can lead to stress and bad behavior.

Cats have often been observed rubbing their faces on objects, individuals or in specific territories for the purposes of marking individuals in their territory or objects. Cats have greatly enlarged sebaceous glands around their mouths, on their chin, in the ear canals in the perianal area and on the tail. When rubbing these areas of the body on objects or individuals they leave a chemical scent behind, which is reassuring to the cat.

Cat's also have a Jacobsen's organ or vomeronasal organ, which is located in the hard palate of the mouth and the septum of the nose. This organ contains duels which lead to the mouth and to the nose. This organ provides a scent analyzer for the cat and it is primarily used to analyze pheromones from other cats. The scent is collected in the cat's mouth where it uses its tongue to flick the scent up to the vomeronasal organ. The upper lip will curl up and the mouth will be partially open. This gesture is known as the Flehmen response, a German word that means "lip curl."

Pheromones are substances released by the body of particular species that cause a predictable reaction by another individual of the same species, which may serve, for example, as a specific attractant, social communicator, sexual stimulant, appeasement and effects basic animal behavior. There are different types of pheromones such as aggregation pheromones that function in defense against predators, mate selection and overcoming host resistance by massive attack; alarm pheromones, which are released when attacked by a predator; epideictic pheromones, which are recognized by insects for signaling other insect that they should clutch elsewhere; releaser pheromones, which are attractant pheromones that some organisms use to attract mates from a distant of two miles or more; signal pheromones, which cause short term changes such as releasing a neurotransmitter which activates a response; primer pheromones, which trigger a change of developmental events; territorial pheromones, which mark the boundary of an animal's territory; trail pheromones, prevalent in insects, such as ants that lay down pheromones as they return to their nest with food; information pheromones, which are indicative of an animal's identity or territory; sex pheromones, which indicate the availability of the female for breeding; cats' facial pheromones that prevents cats from urinating on a marked spot or to prevents anxiety in cats or to familiarize cats in a new environment; and appeasement pheromones, which decrease stress, anxiety and aggressiveness in animate.

In 1977 Silverstein described that semiochemicals and pheromones are multicompound mixtures(Silverstein, R. M.(1977) "Complexity, diversity and specificity of behavior-modifying chemicals; examples from Coleoptera and Hymanoptera," *Chemical Control of Insect Behavior: Theory and Application.* Editors H. H. Shorey & J. J. McKelvey pp. 231 -251 New York: Plenum Press). Pheromones are known to be intraspecific semiochemicals. (Wyatt T. D. (2003) "Pheromones and Animal Behavior. Communication by smell and taste," pp. 1-4 New York: Cambridge University Press).

U.S. Pat. No. 5,709,863 discloses a composition comprising an emulsion comprising a mixture of oleic acid, azaleic acid, pimelic acid, and palmitic acid, said mixture capable of preventing cats from urinating in a marked spot; and a compound of vegetal origin that has an attractive effect on cats. It is not an appeasing pheromone even though it can act in some instances to have a calming effect on cats thus treating a cat's anxiety.

U.S. Pat. Nos. 6,054,481, 6,077,867, 6,169,113, 6,384, 252 and 7,723,388 all describe various mammalian and avian appeasing pheromones. However, none of these patents describe appeasing pheromones for cats.

Thus it is an object of the present invention to provide a novel composition that contains a cat appeasing pheromone.

It is another object of the present invention to provide a solution comprising a cat appeasing pheromone as a spot-on formulation of long duration.

In yet another object a method is provided to appease and/or effect social facilitation in cats.

These and other objects are achieved by the present invention as evidenced by the summary of the invention, the description of the preferred embodiments and the claims.

SUMMARY OF THE INVENTION

The present invention provides a composition comprising a cat appeasing pheromone comprising methyl palmitate, methyl linoleate, methyl oleate, methyl stearate, methyl laurate and methyl myristate, salts thereof, derivatives thereof, isomers thereof and/or structural analogues thereof that maintain the pheromonal appeasement activity and/or social facilitation activity.

Mixtures of methyl palmitate, methyl linoleate, methyl oleate, methyl stearate, methyl laurate and methyl myristate, salts thereof, derivatives thereof, isomers thereof and/or structural analogues thereof that maintain the pheromonal appeasement activity and/or social facilitation activity are also encompassed in the composition of the present invention.

In one aspect a composition comprising between 15% to 25% (w %/w %) methyl palmitate, between 10% to 27% (w %/w %)olethyl linoleate, between 25% to 35% (w %/w %)methyl oleate, between 5% to 15% (w %/w %)methyl stearate, between 5% to 15% (w %/w %)methyl laurate and between 5% to 15% (w %/w %)methyl myristate, salts thereof, derivatives thereof, isomers thereof and/or structural analogues thereof that maintain the pheromonal appeasement activity and/or social facilitation activity is also disclosed.

In another aspect a composition comprising a mixture of between 15% to 25% (w %/w %) methyl palmitate, between 10% to 27% (w %/w %) methyl linoleate, between 25% to 35% (w %/w %) methyl oleate, between 5% to 15% (w %/w %) methyl stearate, between 5% to 15% (w %/w %) methyl laurate and between 5% to 15% (w %/w %) methyl myristate, salts thereof, derivatives thereof, isomers thereof and/or structural analogues thereof that maintain the pheromonal appeasement activity and/or social facilitation activity is also disclosed.

In yet another aspect a composition is provided that comprises between 19% to 26% (w %/w %) methyl palmitate, between 14% to 20% (w %/w %) methyl linoleate, between 26% to 32% (w %/w %) methyl oleate, between 8% to 14% (w %/w %) methyl stearate, between 8% to 14% (w %/w %)methyl laurate and between 8% to 14% (w %/w %) methyl myristate, salts thereof, derivatives thereof, isomers thereof and/or structural analogues thereof that maintain the pheromonal appeasement activity and/or social facilitation activity.

In still another aspect a composition is provided that comprises a mixture of between 19% to 26% (w %/w %) methyl palmitate, between 14% to 20% (w %/w %) methyl linoleate, between 25% to 32% (w %/w %) methyl oleate, between 8% to 14% (w %/w %) methyl stearate, between 8% to 14% (w %/w %) methyl laurate and between 8% to 14% (w %/w %) methyl myristate, salts thereof, derivatives thereof, isomers thereof and/or structure analogies thereof that maintain the pheromonal appeasement activity and/or social facilitation activity.

The compositions, as described herein, can further comprise an acceptable vehicle. This acceptable vehicle is a pharmaceutical acceptable vehicle or a veterinarian acceptable vehicle. The compositions can also contain a nontoxic filler or an enhancer composition. This nontoxic flier can be fatty acids, alcohols, amines, squalene, glycerol and mixtures thereof. The enhancer composition contains volatile organic compounds and mixtures thereof such as amines and fatty acids from indolic derivatives, esters of these amines and fatty acids, ketones such as acetone, alcohols, sterols and the like.

A spot-on composition for the treatment of stress, anxiety, aggressiveness and/or social facilitation in a cat comprising methyl palmitate, methyl linoleate, methyl oleate, methyl stearate, methyl laurate and methyl myristate, salts thereof, derivatives thereof, isomers thereof and/or structural analogues thereof that maintain the pheromonal appeasement activity and/or social facilitation activity and an acceptable vehicle for localized percutaneous application to the cat is also provided by the present invention.

In another aspect a spot-on composition for the treatment of stress, anxiety, aggressiveness and/or social facilitation in a cat comprises between 15% to 25% (w %/w %) methyl palmitate, between 10% to 27% (w %/w %) methyl linoleate, between 25% to 35% (w %/w %) methyl oleate, between 5% to 15% (w %/w %) methyl stearate, between 5% to 15% (w %/w %) methyl laurate and between 5% to 15% (w %/w %) methyl myristate, salts thereof, derivatives thereof, isomers thereof and/or structural analogues thereof that maintain the pheromonal appeasement activity and/or social facilitation activity.

In another aspect the spot-on compositions comprise between 19% to 26% (w %/w %) methyl palmitate, between 14% to 20% (w %/w %) methyl linoleate, between 26% to 32% (w %/w %) methyl oleate, between 8% to 14% (w %/w %)methyl stearate, between 8% to 14% (w %/w %) methyl laurate and between 8% to 14% (w %/w %) methyl myristate, salts thereof, derivatives thereof isomers thereof and/or structural analogues thereof that maintain the pheromonal appeasement activity and/or social facilitation activity.

A spot-on composition comprising 22% (w %/w %) methyl palmitate, 17% (w %/w %) methyl linoleate, 28% (w %/w %) methyl oleate, 11% (w %/w %) methyl stearate, 11% (w %/w %) methyl laurate and 11% (w %/w %) methyl myristate, salts thereof, derivatives thereof, isomers thereof and/or structural analogues thereof that maintain the pheromonal appeasement activity and/or social facilitation activity is yet another aspect of the invention.

Mixtures of the methyl ester fatty acids, as described herein, salts thereof, derivatives thereof, isomers thereof and/or structural analogues thereof that maintain the pheromonal appeasement activity and/or social facilitation activity can also be used in the spot-on compositions with an acceptable vehicle for localized percutaneous application to the cat.

The vehicle for localized percutaneous application to the cat is a glycol ether, which can be diethylene glycol monoethyl ether, diethylene glycol monomethyl ether, diethylene glycol monopropyl ether, diethylene glycol monoisopropyl ether, diethylene glycol monobutyl ether, diethylene glycol monophenyl ether, diethylene glycol monobenzyl ether, diethylene glycol dimethyl ether, ethylene glycol monomethyl ether, ethylene glycol monoethyl ether, ethylene glycol monopropyl ether, ethylene glycol monoisopropyl ether, ethylene glycol monobutyl ether, ethylene glycol monophenyl ether, ethylene glycol monobenzyl ether or ethylene glycol dimethyl ether.

The spot-on composition can also contain a nontoxic filler such as fatty acids, alcohols, amines, squalene, glycerol and mixtures thereof or an enhancer composition such as volatile organic compounds and mixtures thereof such as amines and fatty acids from indolic derivatives, esters of these amines and fatty adds, ketones such as acetone, alcohols, sterols and the like.

A method for treating stress, anxiety and aggressiveness in a cat and/or for treating social facilitation in a cat is also provided, said method comprising administering to said cat the composition, as described herein, or said spot-on composition, as described herein. In these methods the spot-on is administered each fourteen days.

In yet another aspect a composition or a spot-on composition comprising a cat appeasing pheromone comprising methyl palmitate, methyl linoleate, methyl oleate, methyl stearate, methyl laurate and methyl myristate, salts thereof, derivatives thereof, isomers thereof and/or structural analogues thereof that maintain the pheromonal appeasement activity and/or social facilitation activity for use in treating stress, anxiety and aggressiveness in cats and/or to treat social facilitation in cats is provided.

BRIEF DESCRIPTION OF THE DRAWINGS

FIG. 3 is a diagram outlining the experiments performed in Example 3. Five phases existed during this study. Phase 0 when the cats were prepared and treated with the cat appeasing pheromone or a placebo. Phase 1 when the cages were open and the cats were liberated in the corridor and let roam for 5 minutes. Phase 2 when the cats were observed in the corridor. Phase 3, the introduction of a conflict of interest, which consisted of a bowl of cat food. Phase 4, in which the cats were observed with the conflict of interest and Phase 5 where the food was taken away and the cats were observed. These observations were filmed and evaluated by two observers.

DETAILED DESCRIPTION OF THE PREFERRED EMBODIMENTS OF THE INVENTION

As used herein the word "cat" encompasses any member of the family Felidae including the common domestic cats as well as feral cats, tigers, lions, leopards, mountain lions, lynx, bobcats, cheetahs, ocelots and the like.

By "pheromone" is meant a substance released by the body of a particular species that causes a predicted reaction by another individual of the same species, which substance can serve as an attractant social communicator, appeaser, sexual stimulant and the like. In the case of the cat appeasing pheromone, as described herein, besides appeasing the cat from, strenuous and unfamiliar conditions it also has the advantage of targeting social facilitation.

By "social facilitation" is meant that cats that live together in a household are familiar, affiliated and friendly with one another and share a group scent.

"Appeasing pheromone," as used herein, means a pheromone that calms, sooths or relieves stress, anxiety and aggressiveness in cats.

By "stress-associated disease," as used herein, is meant any disease whose symptoms increase due to stress.

"Appeasing effect," as used herein, is meant a reduction of fear, apprehension, anxiety, as well as the behavioral and physical consequences associated with stress and/or social facilitation. The behavioral consequences associated with stress include tremor, vocalization, visual signaling, aggression, displacement activities and the like. The physical consequences associated with stress include changes in heart rate, changes in levels of epinephrine, norepinephrine, ACTH, cortisol, glucose and the like.

As used herein by "structural analogues" is meant any compound that has a structure similar to that of another but differs in one or more functional groups, atoms, or substructures which are replaced with other functional groups, atoms, or substructures. For instance, replacement of methyl groups with heteroatoms in the fatty acids, described herein.

"Derivatives" as used herein include esters, alcohols, ketones, amides, ethers, aldehydes and sterols of the methyl esters of the fatty acids of palmitate, linoleate, oleate, stearate, laureate, myristate, as well as salts thereof and/or structural analogs thereof end mixtures of methyl esters of the fatty acids of palmitate, linoleate, oleate, stearate, laureate, myristate, as well as structural analogs thereof and/or sells thereof. These methylated fatty acid derivatives can replace one or more of the fatty acids in the composition, as described herein, and have the same effects.

"Isomers" includes structural isomerism and spatial isomerism and refers to the methyl esters of the fatty acids of palmitate, linoleate, oleate, stearate, laureate, myristate, as well as salts thereof, derivatives thereof and/or structural analogs that maintain the pheromonal appeasement activity and/or social facilitation activity thereof and mixtures of methyl esters of the fatty acids of palmitate, linoleate, oleate, stearate, laureate, myristate, as well as structural analogs thereof that maintain the pheromonal appeasement activity and/or social facilitation activity, salts thereof and/or derivatives thereof.

As used herein the term "mixtures" encompasses the methyl esters of the fatty acids of palmitate, linoleate, oleate, stearate, laurate, myristate, as well as salts thereof, derivatives thereof, isomers thereof and/or structural analogs thereof that maintain the pheromonal appeasement activity and/or social facilitation activity in which the methyl esters of the fatly acids, as described herein, can be replaced with their salts and/or derivatives and/or isomers and/or structural analogs thereof that maintain the pheromonal appeasement activity and/or social facilitation activity. For example, the mixture can comprise the methyl ester of palmitate and the methyl ester of linoleate, derivatives of oleate and stearate, an isomer of methyl laurate and a structural analogue of myristate.

By "enhancer composition" is meant an active pheromonal composition that is species-species specific in cats and which can be used to enhance or act synergistically with the cat appeasing pheromonal composition to increase the effectiveness in the specific species of the composition.

The term "solution" is meant a solid or oil that is dispersed in a liquid either by being dissolved or in suspension.

"Spot-on" formulations are those for topical delivery of the cat appeasing pheromone to a limited area of cats where it is absorbed percutaneously. These spot-on formulations do not cause irritancy or toxicity to the cats. These spot-on formulations when applied locally to cats will diffuse over the entire body of the cat and then dry without crystallizing. These formulations when dry do not affect the appearance of the cat's fur by making it sticky or leaving crystals.

By "acceptable vehicle" is meant any pharmaceutically acceptable vehicle or veterinary vehicle that does not interfere with the activity of the cat appeasing pheromone composition and is not toxic to the cats to which it is administered. It includes solvents, dispersion media, absorption delaying agents and the like. These pharmaceutically acceptable vehicles are described in Remington's Pharmaceutical Sciences $21^{st}$ edition 2005. An acceptable vehicle can be, for example, glycol ethers. It can be added to the cat appeasing pheromone during formulation.

By "consisting essentially of" means that the compositions contain ail of the methyl ester fatty acids, as described herein, as well as other additives that do not affect the semiochemical nature of the compositions.

More specifically, the present invention relates to the identification of a cat appeasing pheromone that is derived from skin secretions from around the area of the shoulder blades to the head by the ears of cats. These compositions are made up of volatile molecules, the essential components being fatty acid methyl esters comprising methyl palmitate, methyl linoleate, methyl oleate, methyl stearate, methyl laurate and methyl myristate, salts thereof and/or structural analogues thereof that maintain the pheromonal appeasement activity and/or social facilitation activity.

In one aspect a composition is provided that comprises a cat appeasing pheromone comprising methyl palmitate, methyl linoleate, methyl oleate, methyl stearate, methyl laurate methyl myristate, salts thereof, derivatives thereof, isomers thereof, and/or structural analogues thereof that maintain the pheromonal appeasement activity and/or social facilitation activity.

Mixtures of methyl palmitate, methyl linoleate, methyl oleate, methyl stearate, methyl laurate and methyl myristate, salts thereof, derivatives thereof, isomers thereof and/or structural analogues thereof that maintain the pheromonal appeasement activity and/or social facilitation activity are also encompassed in the composition of the present invention.

In one aspect the compositions comprise between 15% to 25% (w %/w %) methyl palmitate, between 10% to 27% (w %/w %) methyl linoleate, between 25% to 35% (w %/w %) methyl oleate, between 5% to 15% (w %/w %) methyl stearate, between 5% to 15% (w %/w %) methyl laurate and between 6% to 15% (w %/w %) methyl myristate, salts thereof, derivatives thereof. Isomers thereof and/or structural analogues thereof that maintain the pheromonal appeasement activity and/or social facilitation activity.

Mixtures of between 15% to 25% (w %/w %) methyl palmitate, between 10% to 27% (w %/w %) methyl linoleate, between 25% to 35% (w %/w %) methyl oleate, between 5% to 15% (w %/w %) methyl stearate, between 5% to 15% (w %/w %) methyl laurate and between 5% to 15% (w %/w %) methyl myristate, salts thereof, derivatives thereof, isomers thereof and/or structural analogues thereof that maintain the pheromonal appeasement activity and/or social facilitation activity also form part of the compositions of the present invention.

In another aspect the compositions comprise between 19% to 26% (w %/w %) methyl palmitate, between 14% to 20% (w %/w %) methyl linoleate, between 26% to 32% (w %/w %) methyl oleate, between 8% to 14% (w %/w %) methyl stearate, between 8% to 14% (w %/w %) methyl laurate and between 8% to 14% (w %/w %) methyl myristate, salts thereof, derivatives thereof, isomers thereof and/or structural analogues thereof that maintain the pheromonal appeasement activity and/or social facilitation activity.

In another aspect the present invention relates to mixtures of between 19% to 26% (w %/w %) methyl palmitate, between 14% to 20% (w %/w %) methyl linoleate, between 25% to 32% (w %/w %) methyl oleate, between 8% to 14% (w %/w %) methyl stearate, between 8% to 14% (w %/w %) methyl laurate and between 8% to 14% (w %/w %) methyl myristate, salts thereof, derivatives thereof, isomers thereof and/or structural analogues thereof that maintain the pheromonal appeasement activity and/or social facilitation activity.

A composition comprising 22% (w %/w %) methyl palmitate, 17% (w %/w %) methyl linoleate, 28% (w %/w %) methyl oleate, 11% (w %/w %) methyl stearate, 11% (w %/w %) methyl laurate and 11% (w %/w %) methyl myristate, salts thereof, derivatives thereof, isomers thereof and/or structural analogues thereof that maintain the pheromonal appeasement activity or social facilitation activity is yet another aspect of the invention.

A composition comprising a mixture of 22% (w %/w %) methyl palmitate, 17% (w %/w %) methyl linoleate, 28% (w %/w %) methyl oleate, 11% (w %/w %) methyl stearate, 11% (w %/w %) methyl laurate and 11% (w %/w %) methyl myristate, salts thereof, derivatives thereof, isomers thereof and/or structural analogues thereof that maintain the pheromonal appeasement activity or social facilitation activity is encompassed by the present invention.

More specifically, the cat appeasing pheromone composition of the present invention comprises a mixture of methyl palmitate methyl linoleate, methyl oleate, methyl stearate, methyl laurate, methyl myristate, salts as well as their structural analogues, which represents between 85% to 95% (wt %/wt %) of the total composition, the remaining ingredients being nontoxic filler compounds such as fatty acids, alcohols, amines, squalene and glycerol. More particularly, aproic acid, azelaic acid, propanoic acid, geraniol, octadecatrianol, hexacosanol, trimethyl amine and methyl amine can be used as the nontoxic fillers.

An enhancer composition comprising between 5% to 36% (w %/w %) can also be added to the pheromonal composition, if desired. This enhancer composition comprises volatile organic compounds and mixtures thereof. This enhancer may be species-species specific in nature. The compounds that can be used in the enhancer composition include, but are net limited to amines and fatty acids from indolic derivatives, esters of these amines and fatty acids, ketones such as acetone, alcohols, sterols and the like.

The pharmaceutically acceptable salts of the cat pheromonal compositions that are used in the compositions, described herein, include those that are organic or inorganic salts of the fatty acid esters of methyl palmitate, methyl linoleate, methyl oleate, methyl stearate, methyl laurate and methyl myristate. These are well known and described in the Physician's Desk Reference. The Merck index and Goodman and Gilman's The Pharmacological Basis of Therapeutics. The pharmaceutically acceptable salts are, for example, sodium, potassium, ammonium, calcium and magnesium and salts formed with inorganic acids such as hydrochloric acid, hydrobromic acid, phosphoric acid, sulfuric acid and the like or salts formed with organic acids such as oxalic acid, tumeric acid, tartaric acid, malonic acid, acetic acid, citric and, benzoic acid and the like.

The compositions can also comprise an acceptable vehicle. This acceptable vehicle can be a pharmaceutically acceptable vehicle or a veterinarian acceptable vehicle. The pharmaceutically acceptable vehicle can be any acceptable carrier or vehicle that does not interfere with the pharmaceutical or veterinary activity of the composition and is not toxic to cats to it is administered. It includes solvents, dispersion media, coatings, absorption delaying agents and the like. These pharmaceutical acceptable vehicles are described in Remington's Pharmaceutical Sciences $22^{nd}$ edition 2012. An acceptable vehicle can be, for example, saline, buffered saline and the like. It can be added to the composition after its formulation.

A spot-on composition for the treatment of stress, anxiety, aggressiveness and/or social facilitation in a cat said spot-on composition comprising: methyl palmitate, methyl linoleate, methyl oleate, methyl stearate, methyl laurate, methyl myristate, salts thereof, derivatives thereof, isomers thereof and structural analogues thereof that maintain the pheromonal appeasement activity or social facilitation activity and a vehicle for localized percutaneous application to the cat forms part of the present invention.

In one aspect the spot-on compositions comprise between 15% to 25% (w %/w %) methyl palmitate, between 10% to 27% (w %/w %) methyl linoleate, between 25% to 35% (w %/w %) methyl oleate, between 5% to 15% (w %/w %) methyl stearate, between 5% to 15% (w %/w %) methyl laurate and between 5% to 15% (w %/w %) methyl myristate, salts thereof, derivatives thereof isomers thereof and/or structural, analogues thereof that maintain the pheromonal appeasement activity and/or social facilitation activity.

The spot-on compositions can also comprise mixtures of between 15% to 25% (w %/w %) methyl palmitate, between 10% to 27% (w %/w %) methyl linoleate, between 25% to 35% (w %/w %) methyl oleate, between 5% to 15% (w %/w %) methyl stearate, between 5% to 15% (w %/w %) methyl laurate and between 5% to 15% (w %/w %) methyl myristate, salts thereof, derivatives thereof, isomers thereof and/or structural analogues thereof that maintain the pheromonal appeasement activity and/or social facilitation activity.

In another aspect the spot-on compositions comprise between 19% to 26% (w %/w %) methyl palmitate, between 14% to 20% (w %/w %) methyl linoleate, between 26% to 32% (w %/w %) methyl oleate, between 8% to 14% (w %/w %) methyl stearate, between 8% to 14% (w %/w %) methyl laurate and between 8% to 14% (w %/w %) methyl myristate, salts thereof, derivatives thereof, isomers thereof and/or structural analogues thereof that maintain the pheromonal appeasement activity and/or social facilitation activity.

The spot-on compositions can comprise mixtures of between 19% to 26% (w %/w %) methyl palmitate, between 14% to 20% (w %/w %) methyl linoleate, between 26% to 32% (w %/w %) methyl oleate, between 8% to 14% (w %/w %) methyl stearate, between 8% to 14% (w %/w %) methyl laurate and between 8% to 14% (w %/w %) methyl myristate, salts thereof, derivatives thereof isomers thereof and/or structural analogues thereof that maintain the pheromonal appeasement activity and/or social facilitation activity.

A spot-on composition comprising 22% (w %/w %) methyl palmitate, 17% (w %/w %) methyl linoleate, 28% (w %/w %) methyl oleate, 11% (w %/w %) methyl stearate, 11% (w %/w %) methyl laurate and 11% (w %/w %) methyl myristate, salts thereof, derivatives thereof, isomers thereof and/or structural analogues thereof that maintain the pheromonal appeasement activity and/or social facilitation activity is yet another aspect of the invention.

Also encompassed by the present invention are spot-on compositions comprising mixtures of 22% (w %/w %) methyl palmitate, 17% (w %/w %) methyl linoleate, 28% (w %/w %) methyl oleate, 11% (w %/w %) methyl stearate, 11% (w %/w %) methyl laurate and 11% (w %/w %) methyl myristate, salts thereof and/or structural analogues thereof that maintain the pheromonal appeasement activity and/or social facilitation activity.

In the spot-on composition, as described herein, the vehicle for localized percutaneous application to the cat is a glycol ether. The glycol ethers that can be used in the spot-on formulations, as described herein include diethylene glycol monoethyl ether, diethylene glycol monomethyl ether, diethylene glycol monopropyl ether, diethylene glycol monoisopropyl ether, diethylene glycol monobutyl ether, diethylene glycol monophenyl ether, diethylene glycol monobenzyl ether, diethylene glycol dimethyl ether, ethylene glycol monomethyl ether, ethylene glycol monoethyl ether, ethylene glycol monopropyl ether, ethylene glycol monoisopropyl ether, ethylene glycol monobutyl ether, ethylene glycol monophenyl ether, ethylene glycol monobenzyl ether or ethylene glycol dimethyl ether. In one embodiment the glycol ether that is used in the spot-on formulation is diethylene glycol monoethyl ether, also known as transcutol®.

A spot-on composition comprising a cat appeasing pheromone comprising methyl palmitate, methyl linoleate, methyl oleate, methyl stearate, methyl laurate and methyl myristate, salts thereof, derivatives thereof, isomers thereof and/or structural analogues thereof that maintain the pheromonal appeasement activity and/or social facilitation activity for use to treat stress, anxiety and aggressiveness in cats is another aspect of the invention.

A spot-on composition comprising a cat appeasing pheromone comprising mixtures of methyl palmitate, methyl linoleate, methyl oleate, methyl stearate, methyl laurate and methyl myristate, salts thereof, derivatives thereof, isomers thereof and/or structural analogues thereof that maintain the pheromonal appeasement activity and/or social facilitation activity for use to treat stress, anxiety end aggressiveness in cats is another aspect of the invention.

In yet another aspect of the invention a spot-on composition comprising a cat appeasing pheromone comprising methyl palmitate, methyl linoleate, methyl oleate, methyl stearate, methyl laurate and methyl myristate, salts thereof, derivatives thereof, isomers thereof and/or structural analogues thereof that maintain the pheromonal appeasement activity and/or social facilitation activity and mixtures thereof for use to treat social facilitation in cats.

The structural analogs are compounds that have a structure similar to methyl palmitate, methyl linoleate, methyl oleate, methyl stearate, methyl laurate and methyl myristate, but differ in one or more atoms or functional groups. Thus, for example, the methyl group in the fatty acids in the compositions and spot-on compositions, disclosed herein, can be replaced by one or more atoms or functional groups.

The spot-on composition can further comprise a nontoxic filler or an enhancer composition. The nontoxic fillers that can be used in the spot-on compositions, as described herein, include fatty acids, alcohols, amines, squalene, glycerol and mixtures thereof. The enhancer compositions contains volatile organic compounds and mixtures thereof such as amines and fatty acids from indolic derivatives, esters of these amines and fatty acids, ketones such as acetone, alcohols, sterols and the like.

In yet another aspect a method for treating stress, anxiety and aggressiveness in a cat by administering to the cat the composition, as described herein, or the spot-on composition, as described herein. The spot-on composition is administered each fourteen days and hence is a long lasting formulation.

A method for treating social facilitation in a cat by administering to the cat the composition, as described herein, or the spot-on composition, as described herein, is yet another embodiment of the invention. The spot-on composition is administered each fourteen days and hence is a long lasting formulation.

The cat appeasing pheromonal composition can be attached to a chemical earner provided that the bioactive structure of the fatty acid methyl esters is preserved. Such carrier molecules include crown compounds, liposomes and carrier proteins.

The compositions, as described herein, can be diluted in various solutions, as set forth below and can be used in various liquid forms.

The composition, as described herein, may be in the form of a liquid carrier that can be applied directly to the cat or that of a spot-on formulation. The spot-on formulations are believed to work by percutaneously penetrating the skin of cats and then distributing in the sebaceous glands of the cat's skin. Thus the sebaceous glands provide a natural reservoir for the cat appeasing pheromone spot-on compositions which allows for the composition to be drained back out to the cats' follicles to reapply to the skin and cat's hair.

The spot-on formulations provide for a topical administration of solutions, concentrated solutions, micellular solutions, microemulsions or combinations thereof for application to a spot on the cat, which is generally between the two shoulders.

The organic solvent for the liquid carrier includes commonly acceptable solvents known in the formulation art such as glycol ethers, as described herein, acetone, ethyl acetate, methanol, ethanol, isopropanol, dimethylformamide, dichloromethane, propylene glycol and the like. These solvents are described in, for example, Remington Pharmaceutical Science, $22^{nd}$ edition (2012).

Solutions and concentrated solutions are well known in the art and have the cat appeasing pheromone dispersed in a liquid either by being dissolved or in suspension. The concentrated solutions contain more solute than dilute solutions.

Micellular solutions are a dispersion of micelles in a solvent. They are generally 2 to 5 nanometers in diameter. They have no long-range positional order but are randomly distributed in the solvent. Microcellular solutions can be used in the compositions or spot-on compositions of the present invention described herein.

Microemulsions can be used in the compositions or spot-on formulations, described herein, which are composed of liquid dispersions of oil and water that are made homogenous, transparent and thermodynamically stable by adding a surfactant and a co-surfactant. Microemulslons are formed when the interfacial tension at the oil/water interface is brought to a very low level and the interfacial layer is kept highly-flexible and fluid. They have diameters ranging in size from 10 to 100 nanometers.

The oily phase in the microemulsion can be formed from vegetable or mineral oils, from unsaturated polyglycosylated glycerides or from triglycerides. The oily phase represents about 2% to 15% v %/v % of the microemulsion.

The aqueous phase in the microemulsion can be, for example, water or glycol derivatives such as propylene glycol, glycol ethers, polyethylene glycols or glycerol and is present in the microemulsion at about 1% to 4% (v %/v %).

Surfactants that can be used include diethylene glycol monoethyl ether, dipropylene glycol monomethyl ether, polyglycolysed $C_8$-$C_{10}$ glycerides. They are present in the microemulsion at about 25% to 75% (v %/V %). The cosurfactants can be short chain alcohols. The cosurfactant is present in the microemulsion in an amount of 10% to 55% (v%/v%).

In the compositions or spot-on compositions, as described herein between about 1.5 g to 2.5 g of the cat appeasing pheromone can be diluted in the acceptable vehicle, as described herein, of about 90 g to 110 g. In another embodiment 2.0 g of cat appeasing pheromone is added to 100 g of transcutol.®

Fatty acid methyl esters are commercially available from various chemical companies. However, since they are difficult to solubilize, the fatty acid methyl ester is generally added to the solvent under constant agitation and at a temperature between about 37° C. to about 38° C. In another aspect the temperature is about 37.5° C.

Once obtained the compositions of the present invention can be tested for their efficacy to prevent stress and/or social facilitation in cats. Well documented stressors are the transportation of cats, moving the cats into a new environment adding an additional oat or cats to the household, moving furniture or buying new furniture that the cats are not acquainted with and the like. Application of the compositions in the form of a solution or a spot-on formulation will result in a diminution of stress in the cat or cats as indicated by their social behavior with respect to other cats, salivary cortisol, heart rate, less aggression with other cats as evidenced by less behavior in which the cats tail is held out and moved from side to side and less vocal communication of aggression with other cats and animals.

The above-described compositions were discovered after detailed analysis of the chemical compositions surrounding the shoulders to the ears of a cat with a sterile compress and analyzing the chemical compositions of the secretions via gas chromatography/mass spectroscopy (GC/MS) and single ion monitoring(SIM). A comparison of the chromatographic GC/MS was undertaken at day 0, at day 14 and at day 28, as well as the SIM analysis.

The initial spectra together with statistical analysis revealed that there were four to six compounds, which were methyl palmitate, methyl linoleate, methyl oleate and methyl stearate were first identified. A complementary analysis using SIM confirmed the additional 2 missing components of methyl laurate and methyl myristate.

In order to further illustrate the present invention and advantages thereof the following specific examples are given it being understood that the same are intended only as illustrative and in nowise limitative.

EXAMPLES

Example 1

Isolation and Analysis of Components in Secretions of Cats

Cat samples were taken from the skin of the cat between the shoulder blades and between the ears by subbing a compress for two minutes. For the analysis at time zero (T0) and day 14 (T14) the compress was rubbed from the shoulder blades to the head of the cat. For the sampling at day 28 (T28) half of the zone from the shoulder blades to the head was rubbed. The compress was then immediately placed in a flask and 4.0 g of dichloromethane was added. With the use of a glass pipette the solvent was collected and the solvent was squirted over the compress. The process was repeated five times. At the end of the fifth washing a sample was collected for chromatographical analysis.

The samples were then subjected to gas chromatography/mass spectroscopy (GC/MS) using a SHIMAZU QP 2010. The detection was effectuated on impact using (EI+) at an energy of 70 eV at 200® CA. A Supelco type DB column was used having a length of 30 m(id=0.25 mm; film=0.25 µm at a split of ½0 and a split/splitless of 1 minute. 2.0 µl from each sample was injected.

The 6C/MS analysis was performed at clay 0(T0), at day 14(T14) and at day 28(T28).

The results were analyzed using a data base to obtain the most probable spectrums. Data bases containing such data are well known in the art.

Figure 1:
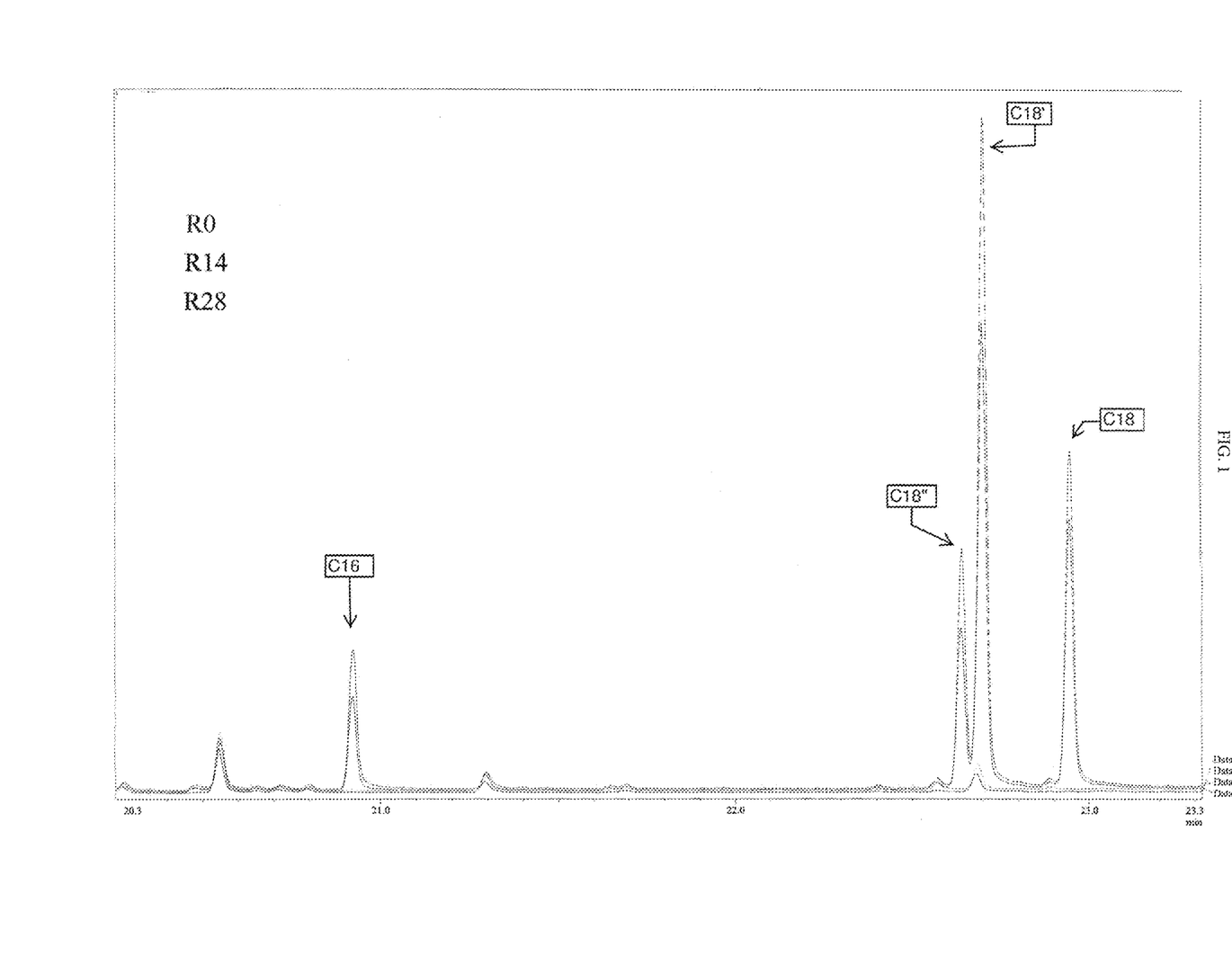
FIG. 1 is a gas chromatograph/mass spectroscopy spectrum profile of the components in the secretion from a cat at Day 0, Day 14 and Day 28. In this profile methyl palmitate, methyl linoleate, methyl oleate and methyl stearate were identified.

Four to six compounds of semiochemicals were discovered upon the GC/MS analysis: methyl palmitate, methyl linoleate, methyl oleate, methyl laurate, methyl myristate and methyl strearate. See, FIG. 1. However, two additional compounds were present that had to be identified that had retention times of 16.25 and 18.71.

Figure 2:
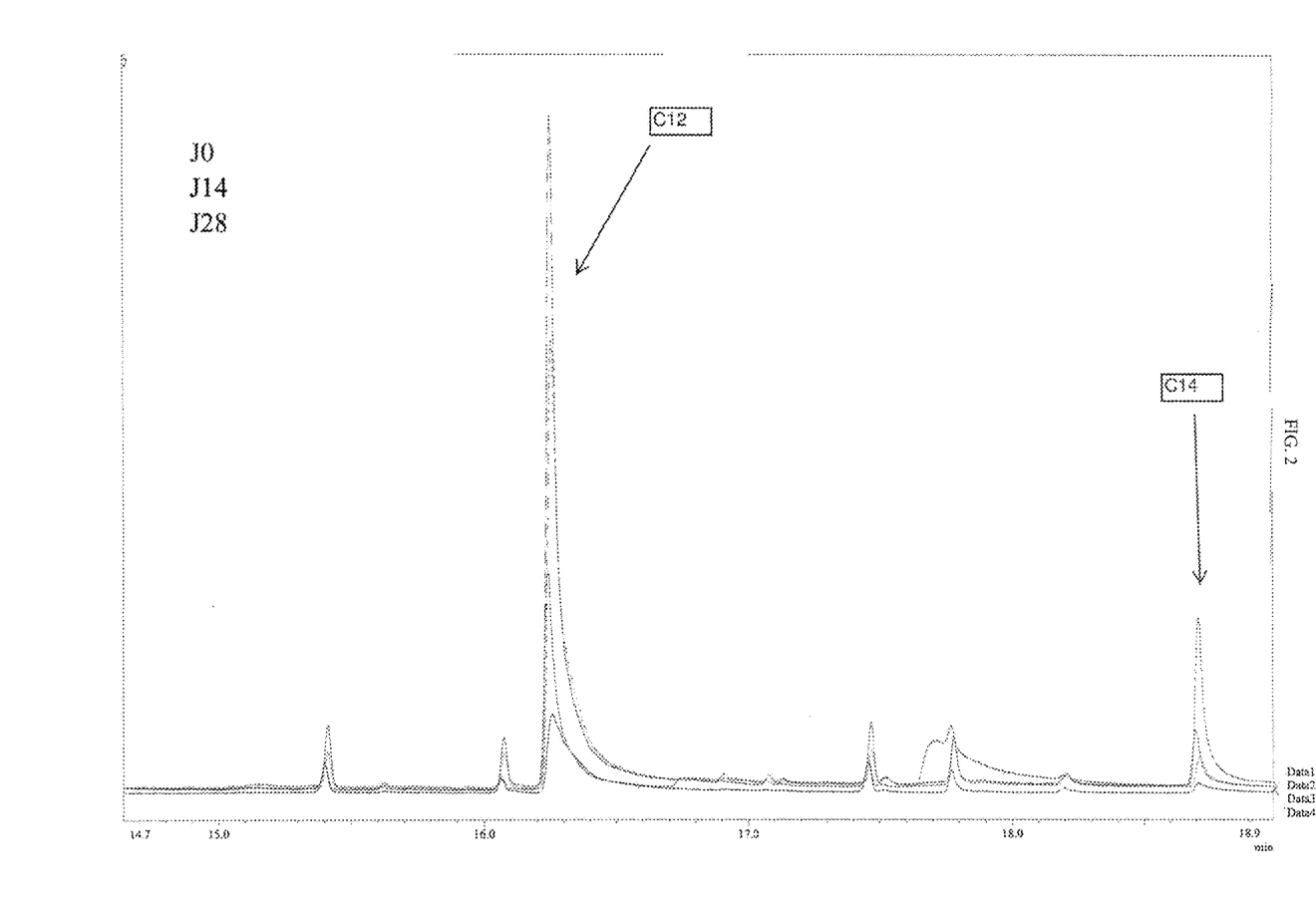
FIG. 2 is a chromatograph taken after single ion monitoring (SIM) of the components in the secretion from a cat at Day 0, Day 14 and Day 28. In this profile methyl palmitate, methyl linoleate, methyl oleate, methyl stearate, methyl laurate and methyl myristate were identified.

To lower the threshold of detection the Single Ion Monitoring technique was used to focus the detection uniquely on the fragments of the molecules that were sought, which were unidentified but had retention times of 16.25 and 18.71. Single ion monitoring was also performed at day 0T0), at day 14(T14) and at day 28(T28).

The chromatographic profile for the Single Ion Monitoring can be found in FIG. 2. Further analysis revealed the presence of the two compounds of methyl laurate and methyl myristate.

Thus, the cat appeasing pheromone is constituted of between 15% to 25% (w %/we %) of methyl palmitate, between 10% to 27% (w %/w %) of methyl linoleate, between 25% to 35% (w %/w %) of methyl oleate, between 5% to 15% (w %/w %) of methyl stearate 5% to 15% (w %/w %) of methyl laurate and between 5% to 15% (w %/w %) of methyl myristate.

Example 2

Formula of the Cat Appeasing Pheromone as a Spot-On

The cat appeasing pheromone as described in Example 1 having six different methyl esters of fatty acids was formulated with transcutol.® 2 grams of cat appeasing pheromone was mixed with 100 grams of transcutol.®

Example 3

Test of the Cat Appeasing Pheromone Against a Placebo

Figure 3:
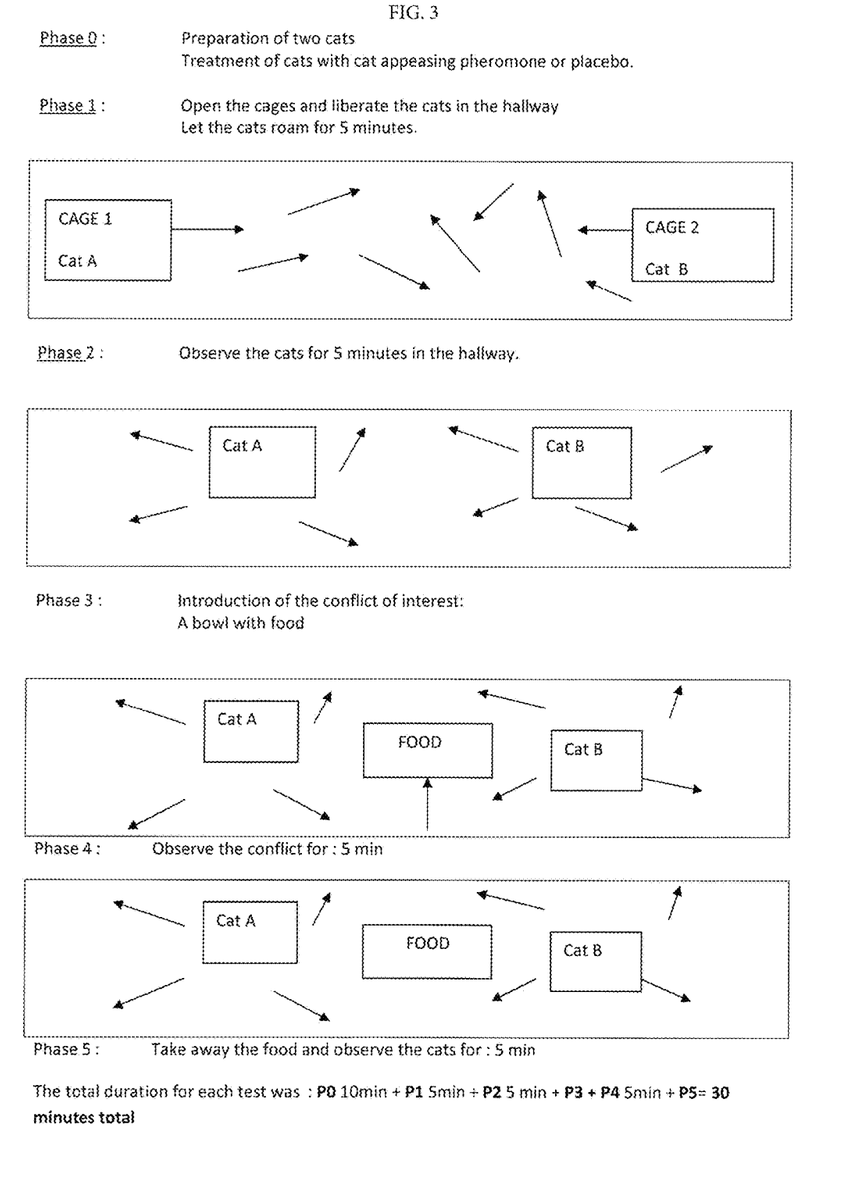

Sixteen cats were obtained for this example. This test had 6 different phases. Phase 0 was to obtain the sixteen cats and treat them with either the placebo or the cat appeasing pheromone (CAP) and lasted 10 minutes. Each experiment was performed using two cats each time. The two cats were placed in two different cages and placed in a corridor. The corridor was 5 meters in length and 1.80 meters in width. The cages were then opened and the cats were left free to roam in the corridor for 5 minutes and their movements were observed during Phase 1. During Phase 2 a preconflict period was observed in which the cats were left alone in the corridor but were observed for 5 minutes. In Phase 3 a conflict of interest was introduced in the corridor consisting of a bowl of food. This bowl was introduced in the middle of the corridor and the cats were observed. In Phase 4 was the start of the postconflict period. Phases 3 and 4 were observed for 5 minutes. In Phase 5 the cat food was removed and the cats were placed in their respective cages and observed for 5 minutes.

The entire experiment lasted a total of 30 minutes and was filmed. It was repeated twenty-four times using different cats. There were two different observers for this example.

Duration Pre-Conflict

The data was calculated using Spearman's rank correlation coefficient. The results are listed below. For the length of preconflict the rho=0.96460 and p<0.0001=>$rho^2$=0.93, thus 93% of a liaison between the two observers. The value of rho is between 0.9 and 1, thus there was a very high correlation between the two observers. The liaison between the observers was reliable and one could conclude that the agreement between the two observers was almost perfect.

Duration Post Conflict

For the duration of the post-conflict, the rho=0.5000 and p=0.0128=>$rho^2$=0.25 thus 25% of a liaison. The value of rho was between 0.4 and 0.7 thus only a moderate correlation between the two observers. The liaison between the two observers was substantial and one cannot conclude with certainty that there was agreement between the two observers.

Frequency Pre-Conflict

For the frequency of pre-conflict the rho=0.94939 and p<1.0001=>$rho^2$=0.90 thus 90% of liaison. The value of rho was between 0.9 and 1 thus a very high correlation between the two observers. The liaison between the observers was reliable and one could conclude that the agreement between the two observers was almost perfect.

Frequency Post-Conflict

For the frequency of post-conflict the rho=0.72232 and p<0.0001=>$rho^2$=0.52 thus 52% of liaison. The value of rho was between 0.7 and 0.9 thus there was a high correlation between the two observers. The liaison is marked and one can conclude that there is good agreement between the two observers.

The conclusion was that the two observers should return to their videos to further evaluate the duration of post-conflict.

The analysis was then undertaken using the non parametric test of Mann Whitney Wilcoxon for the duration post-contact.

Duration Pre-Conflict

| Variable | Mean deviation ± standard type TT1 | Mean deviation ± standard type TT2 | Statistical test | p value | Significant level |
|---|---|---|---|---|---|
| Duration pre-conflict | 24.542 ± 36.599 | 19.25 ± 40.66 | −0.4315 | 0.6661 | NS[1] |

NS[1]: not significant (p ≥ 0.05)
2*significant(0.01 ≤ p < 0.05)
3**very significant(.001 ≤ p < 0.01)
4***highly significant(p < 0.001)

There was no significant difference concerning the duration of the pre-conflict of friendly contact between the two treated groups.

The analysis was then undertaken using the non parametric test of Mann Whitney Wilcoxon for the frequency of pre-contact.

Frequency Pre-Conflict

| Variable | Mean deviation ± standard type TT1 | Mean deviation ± standard type TT2 | Statistical test | P value | Significant level |
|---|---|---|---|---|---|
| Frequency pre-conflict | 0.9167 ± 1.2401 | 0.625 ± 1.4322 | −0.6317 | 0.5276 | NS[1] |

NS[1]: not significant (p ≥ 0.05)
2*significant(0.01 ≤ p < 0.05)
3**very significant(.001 ≤ p < 0.01)
4***highly significant(p < 0.001)

There was no significant difference concerning the frequency of the pre-conflict of friendly contact between the two treated groups.

The analysis was then undertaken using the non parametric test of Mann Whitney Wilcoxon for the frequency of post-contact.

Frequency Post-Conflict

| Variable | Mean deviation ± standard type TT1 | Mean deviation ± standard type TT2 | Statistical test | P value | Significant level |
|---|---|---|---|---|---|
| Frequency pre-conflict | 0.2083 ± 0.5823 | 0 ± 0 | −1.3844 | 0.1662 | NS[1] |

NS[1]: not significant ($p \geq 0.05$)
2*significant($0.01 \leq p < 0.05$)
3**very significant($.001 \leq p < 0.01$)
4***highly significant($p < 0.001$)

There was no significant difference concerning the frequency of the post-conflict of friendly contact between the two treated groups.

This example illustrates that the Cat Appeasing Pheromone group showed an increased duration of affiliative interactions (df=1; Z=1.299; p=1939) and time spent in proximity (df=1; Z=1.645; p=0.0999). The treated Cat Appeasing Pheromone group also had a lower threat rate (df=1; Z=1.506; p=0.1319 compared to the control placebo and that the affiliative interactions were maintained after the conflict of interest introduction (df=11; S=21; p=0.0199).

Example 4

Test of the Cat Appeasing Pheromone Against a Placebo

A second set of testing was performed as in Example 3. Nine tests were performed.

Duration Pre-Conflict

A verification of the reliability of the two observers was undertaken using Spearman's rank correlation coefficient during the duration pre-conflict. The results are listed below. For the duration of preconflict the rho=0.99582 and p<0.0001=>rho$^2$=0.99; thus 99% of a liaison between the two observers. The value of rho is between 0.9 and 1, thus there was a very high correlation between the two observers. The liaison between the observers was reliable and one could conclude that the agreement between the two observers was almost perfect.

Duration Post-Conflict

For the duration of the post-conflict, the rho=0.5000 and p=1.705=>rho$^2$=0.25 thus 25% of a liaison. The value of rho was between 0.4 and 0.7 thus only a moderate correlation between the two observers. The liaison between the two observers was substantial and one cannot conclude with certainty that there was agreement between the two observers and also the difference was non-significant.

Frequency Pre-Conflict

For the frequency of pre-conflict the rho=0.97333 and p<0.0001>rho$^2$=0.95 thus 95% of liaison. The value of rho was between 0.9 and 1 thus a very high correlation between the two observers. The liaison between the observers was reliable and one could conclude that the agreement between the two observers was almost perfect.

Frequency Post-Conflict for the frequency of post-conflict the rho=0.75000 and p<0.0199=>rho$^2$=0.56 thus 56% of liaison. The value of rho was between 0.7 and 0.9 thus there was a high correlation between the two observers. The liaison is marked and one can conclude that there is good agreement between the two observers.

The conclusion was that the two observers should return to their videos to further evaluate the duration of post-conflict.

The analysis was then undertaken using the non parametric test of Mann Whitney Wilcoxon for the duration pre-contact.

Duration Pre-Conflict

| Variable | Mean deviation ± standard type TT1 | Mean deviation ± standard type TT2 | Statistical test | p value | Significant level |
|---|---|---|---|---|---|
| Duration pre-conflict | 58.9 ± 33.971 | 57.75 ± 55.654 | −0.1225 | 0.9025 | NS[1] |

NS[1]: not significant ($p \geq 0.05$)
2*significant($0.01 \leq p < 0.05$)
3**very significant($.001 \leq p < 0.01$)
4***highly significant($p < 0.001$)

There was no significant difference concerning the frequency of the pre-conflict of friendly contact between the two treated groups.

The analysis was then undertaken using the non parametric test of Mann Whitney Wilcoxon for the frequency of pre-contact.

Frequency Pre-Conflict

| Variable | Mean deviation ± standard type TT1 | Mean deviation ± standard type TT2 | Statistical test | p value | Significant level |
|---|---|---|---|---|---|
| Frequency pre-conflict | 2/2 ± 0.8367 | 1.875 ± 2.0966 | −0.8796 | 0.3791 | NS[1] |

NS[1]: not significant ($p \geq 0.05$)
2*significant($0.01 \leq p < 0.05$)
3**very significant($.001 \leq p < 0.01$)
4***highly significant($p < 0.001$)

There was no significant difference concerning the frequency of the pre-conflict of friendly contact between the two treated groups.

The analysis was then undertaken using the non parametric test of Mann Whitney Wilcoxon for the frequency of post-contact.

Frequency Post-Conflict

| Variable | Mean deviation ± standard type TT1 | Mean deviation ± standard type TT2 | Statistical test | P value | Significant level |
|---|---|---|---|---|---|
| Frequency post-conflict | 0.5 ± 0.866 | 0 ± 0 | −1.1739 | 0.2404 | NS[1] |

NS[1]: not significant ($p \geq 0.05$)
2*significant($0.01 \leq p < 0.05$)
3**very significant($.001 \leq p < 0.01$)
4***highly significant($p < 0.001$)

There was no significant difference concerning the frequency of the post-conflict of friendly contact between the two treated groups.

Proximity

Duration Pre-Conflict

A verification of the reliability of the two observers was undertaken using Spearman's rank correlation coefficient during the duration pre-conflict The results are listed below. For the duration of preconflict the rho=0.96804 and p<0.0001=>rho$^2$=0.94, thus 94% of a liaison between the two observers. The value of rho is between 0.9 and 1, thus there was a very high correlation between the two observers. The liaison between the observers was reliable and one could conclude that the agreement between the two observers was almost perfect.

Duration Post-Conflict

For the duration of the post-conflict, the rho=0.97891 and p<0.0001=>rho$^2$=0.96 thus 96% of a liaison. The value of rho was between 0.9 and 1 thus a very high correlation between the two observers. The liaison between the two observers was reliable and one could conclude that the agreement between the two observers almost perfect.

Frequency Pre-Conflict

For the frequency of pre-conflict the rho=0.94412 and p<0.0001=>rho$^2$=0.89 thus 89% of liaison. The value of rho was between 0.9 and 1 thus a very high correlation between the two observers. The liaison between the observers was reliable and one could conclude that the agreement between the two observers was almost perfect.

Frequency Post-Conflict

For the frequency of post-conflict the rho=0.85966 and p<0.0001=>rho$^2$=0.74 thus 74% of liaison. The value of rho was between 0.7 and 0.9 thus there was a high correlation between the two observers. The liaison is marked and on can conclude that there is good agreement between the two observers.

In conclusion all the parameters can be analyzed.

The analysis was then undertaken using the non parametric test of Mann Whitney Wilcoxon for the duration pre-contact.

Duration Pre-Conflict

| Variable | Mean deviation ± standard type TT1 | Mean deviation ± standard type TT2 | Statistical test | p value | Significant level |
|---|---|---|---|---|---|
| Duration pre-conflict | 208.25 ± 81.17 | 276.21 ± 121.1 | 1.6454 | 0.999 | NS[1] |

NS[1]: not significant (p ≥ 0.05
2*significant(0.01 ≤ p < 0.05)
3**very significant(.001 ≤ p < 0.01)
4***highly significant(p < 0.001)

There was no significant difference concerning the frequency of the pre-conflict of friendly contact between the two treated groups.

The analysis was then undertaken using the non parametric test of Mann Whitney Wilcoxon for the duration post-contact.

Duration Post-Conflict

| Variable | Mean deviation ± standard type TT1 | Mean deviation ± standard type TT2 | Statistical test | p value | Significant level |
|---|---|---|---|---|---|
| Duration pre-conflict | 185.67 ± 110.9 | 216.04 ± 104.11 | 0.7794 | 0.4357 | NS[1] |

NS[1]: not significant (p ≥ 0.05
2*significant(0.01 ≤ p < 0.05)
3**very significant(.001 ≤ p < 0.01)
4***highly significant(p < 0.001)

There was no significant difference concerning the frequency of the pre-conflict of friendly contact between the two treated groups.

The analysis was then undertaken using the non parametric test of Mann Whitney Wilcoxon for the frequency pre-conflict.

Frequency Pre-Conflict

| Variable | Mean deviation ± standard type TT1 | Mean deviation ± standard type TT2 | Statistical test | p value | Significant level |
|---|---|---|---|---|---|
| frequency pre-conflict | 6.9583 ± 2.3785 | 5.375 ± 2.1651 | −1.5054 | 0.1322 | NS[1] |

NS[1]: not significant (p ≥ 0.05
2*significant(0.01 ≤ p < 0.05)
3**very significant(.001 ≤ p < 0.01)
4***highly significant(p < 0.001)

There was no significant difference concerning the frequency of the pre-conflict of friendly contact between the two treated groups.

The analysis was then undertaken using the non parametric test of Mann Whitney Wilcoxon for the frequency post-conflict.

Frequency Post-Conflict

| Variable | Mean deviation ± standard type TT1 | Mean deviation ± standard type TT2 | Statistical test | P value | Significant level |
|---|---|---|---|---|---|
| frequency post-conflict | 4.9583 ± 2.4537 | 5.1667 ± 2.4802 | 0.3789 | 0.7047 | NS[1] |

NS[1]: not significant (p ≥ 0.05
2*significant(0.01 ≤ p < 0.05)
3**very significant(.001 ≤ p < 0.01)
4***highly significant(p < 0.001)

There was no significant difference concerning the frequency of the pre-conflict of friendly contact between the two treated groups.

These data are in agreement with those of Example 3 and show that the treated Cat Appeasing Pheromone group showed an increased duration of affiliative interactions, time spent in proximity, a lower threat rate and affiliative interactions were maintained after the conflict of interest introduction.

While the invention has been described in terms of various preferred embodiments, the skilled artisan will appreciate that various modifications, substitutions, omissions and changes may be made without departing from the scope thereof. Accordingly it is intended that the scope of the present invention be limited to the scope of the following claims, including equivalents thereof.

What is claimed is:

1. A composition consisting essentially of a cat appeasing pheromone consisting essentially of methyl palmitate, methyl linoleate, methyl oleate, methyl stearate and methyl myristate, mixtures thereof, salts thereof, isomers thereof and/or structural analogs thereof that maintain the pheromonal appeasement activity and/or social facilitation activity and an acceptable vehicle.

2. The composition according to claim 1, wherein said cat appeasing pheromone consists of between 15% to 25% (w %/w %) methyl palmitate, between 10 to 27% (w %/w %) methyl linoleate, between 25% to 35% (w %/w %) methyl oleate, between 5% to 15% (w %/w %) methyl stearate, between 5% to 15% (w %/w %) methyl laurate and between 5% to 15% (w %/w %) methyl myristate, salts thereof, isomers thereof and/or structural analogs thereof that maintain the pheromonal appeasement activity and/or social facilitation activity.

3. The composition according to claim 1, wherein said cat appeasing pheromone or said mixture in said composition consists of between 19% to 26% (w %/w %) methyl palmitate, between 14% to 20% (w %/w %) methyl linoleate, between 26% to 32% (w %/w %) methyl oleate, between 8% to 14% (w %/w %) methyl stearate, between 8% to 14% (w %/w %) methyl laurate and between 8% to 14%(w %/w %) methyl myristate, salts thereof, isomers thereof and/or structural analogs thereof that maintain the pheromonal appeasement activity and/or social facilitation activity.

4. A spot-on composition for the treatment of stress, anxiety, aggressiveness and social facilitation in a cat said spot-on composition consisting essentially of: methyl palmitate, methyl linoleate, methyl oleate, methyl stearate, methyl laurate and methyl myristate, mixtures thereof, salts thereof, isomers thereof and/or structural analogues thereof that maintain the pheromonal appeasement activity or social facilitation activity and a vehicle for localized percutaneous application to the cat.

5. The spot-on composition according to claim 4, consisting of between 15% to 25% (w %/w %) methyl palmitate, between 10% to 27% (w %/w %) methyl linoleate, between 25% to 35% (w %/w %) methyl oleate, between 5% to 15% (w %/w %) methyl stearate, between 5% to 15% (w %/w %) methyl laurate and between 5% to 15% (w %/w %) methyl myristate, mixtures thereof, salts thereof, derivatives thereof, isomers thereof and/or structural analogues thereof that maintain the pheromonal appeasement activity and/or social facilitation activity and a vehicle for localized percutaneous application to the cat.

6. The spot-on composition according to claim 4, consisting of between 19% to 26% (w %/w %) methyl palmitate, between 14% to 20% (w %/w %) methyl linoleate, between 26% to 32% (w %/w %) methyl oleate, between 8% to 14% (w %/w %) methyl stearate, between 8% to 14% (w %/w %) methyl laurate and between 8% to 14% (w %/w %) methyl myristate, mixtures thereof, salts thereof, derivatives thereof, isomers thereof and/or structural analogues thereof that maintain the pheromonal appeasement activity and/or social facilitation activity and a vehicle for localized percutaneous application to the cat.

7. A spot-on composition consisting essentially of 22% (w %/w %) methyl palmitate, 17% (w %/w %) methyl linoleate, 28% (w %/w %) methyl oleate, 11% (w %/w %) methyl stearate, 11% (w %/w %) methyl laurate and 11% (w %/w %) methyl myristate, mixtures thereof, salts thereof, derivatives thereof, isomers thereof and/or structural analogues thereof that maintain the pheromonal appeasement activity and/or social facilitation activity and a vehicle for localized percutaneous application to the cat.

8. The spot-on composition according to claim 7, wherein said vehicle for localized percutaneous application to the cat is a glycol ether or diethylene glycol monoethyl ether, diethylene glycol monoethyl ether, diethylene glycol monomethyl ether, diethylene glycol monopropyl ether, diethylene glycol monoisopropyl ether, diethylene glycol monobutyl ether, diethylene glycol monophenyl ether, diethylene glycol monobenzyl ether, diethylene glycol dimethyl ether, ethylene glycol monomethyl ether, ethylene glycol monoethyl ether, ethylene glycol monopropyl ether, ethylene glycol monoisopropyl ether, ethylene glycol monobutyl ether, ethylene glycol monophenyl ether, ethylene glycol monobenzyl ether or ethylene glycol dimethyl ether.

9. A method for treating stress anxiety and aggressiveness in a cat or for treating social facilitation in a cat said method comprising administering to said cat the composition of claim 1.

10. The method according to claim 9, wherein said composition is administered each fourteen days.

11. A method for treating stress anxiety and aggressiveness in a cat or for treating social facilitation in a cat said method comprising administering to said cat the composition of claim 4.

12. The method according to claim 11, wherein said spot-on composition is administered each fourteen days.

* * * * *